(12) United States Patent
Alchas et al.

(10) Patent No.: US 7,674,242 B2
(45) Date of Patent: *Mar. 9, 2010

(54) INTRADERMAL NEEDLE

(75) Inventors: Paul G. Alchas, Wayne, NJ (US);
Marina S. Korisch, Wayne, NJ (US);
Peter W. Heyman, Florham Park, NJ (US); John Laiosa, Lodi, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/774,666

(22) Filed: Jul. 9, 2007

(65) Prior Publication Data
US 2007/0255225 A1 Nov. 1, 2007

Related U.S. Application Data

(63) Continuation of application No. 10/456,001, filed on Jun. 6, 2003, now Pat. No. 7,241,275, which is a continuation-in-part of application No. 09/834,438, filed on Apr. 13, 2001, now Pat. No. 6,843,781, which is a continuation-in-part of application No. 09/417,671, filed on Oct. 14, 1999, now Pat. No. 6,494,865.

(51) Int. Cl.
*A61M 5/00* (2006.01)

(52) U.S. Cl. ..................................... 604/117
(58) Field of Classification Search ............. 604/93.01, 604/116–117, 192, 198, 240–242; 220/4.01, 220/4.04–4.07
See application file for complete search history.

(56) References Cited

U.S. PATENT DOCUMENTS 5,873,856 A * 2/1999 Hjertman et al. ............ 604/117
7,241,275 B2 * 7/2007 Alchas et al. ............... 604/117

* cited by examiner

*Primary Examiner*—Kevin C Sirmons
*Assistant Examiner*—Deanna K Hall
(74) *Attorney, Agent, or Firm*—Robert E. West

(57) ABSTRACT

An intradermal needle comprising a needle cannula assembly having a limiter portion, a hub portion and a needle cannula, a protective cap having a forward and rearward cap to protect and shield a needle cannula prior to and after use, and means for engaging the needle cannula assembly and the rearward cap after use. The mated forward and rearward cap provide a sterile enclosure for the needle cannula assembly prior to use. Removing the rearward cap permits the needle cannula assembly to be coupled to a drug delivery device, while the forward cap removably shields the needle cannula. Removing the forward cap then exposes the needle cannula for use. After use, the distal end of the needle cannula assembly is placed into the rearward cap and lockingly engaged therewith.

10 Claims, 6 Drawing Sheets

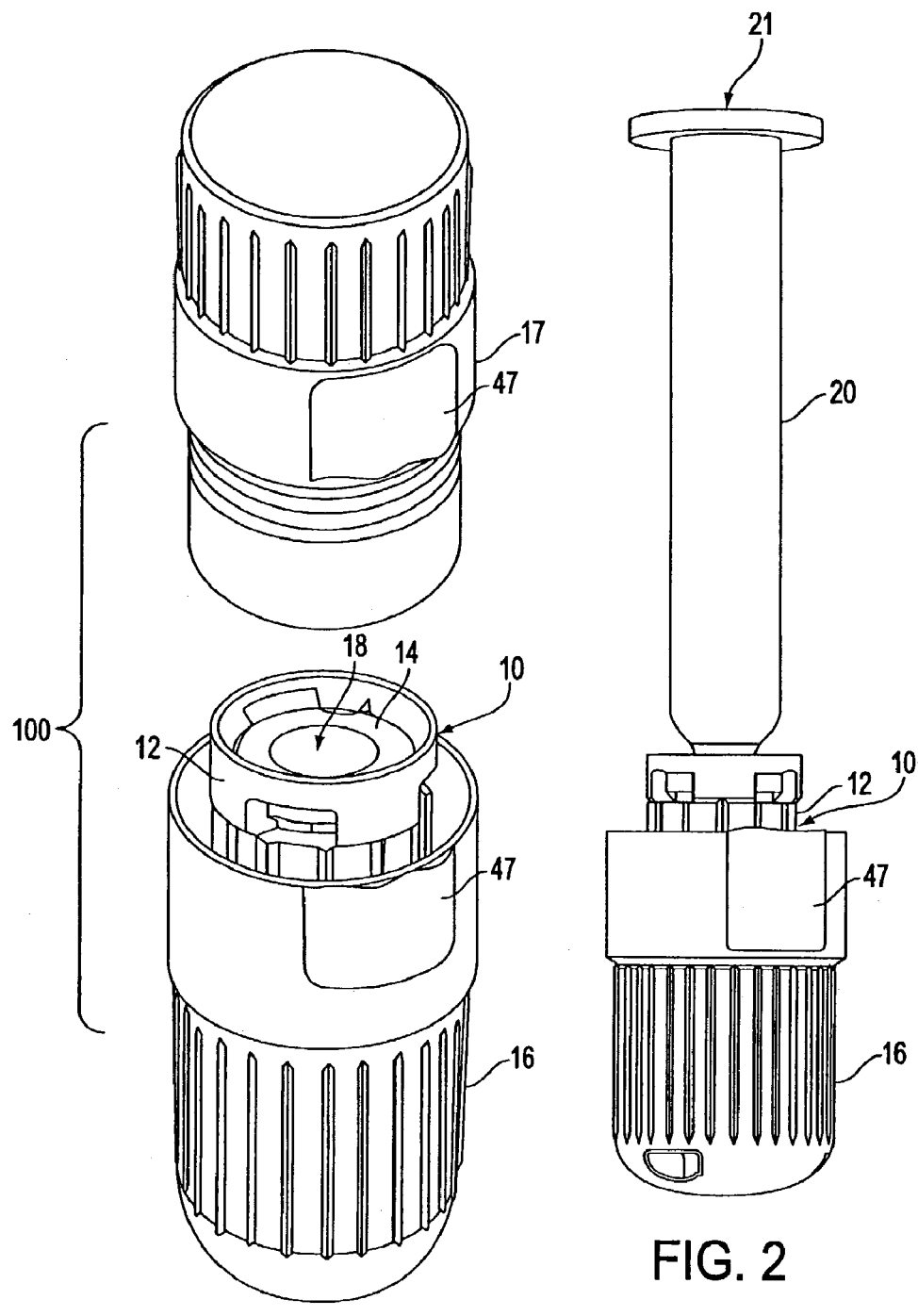

INTRADERMAL NEEDLE

The present application is a continuation of U.S. patent application Ser. No. 10/456,001, filed Jun. 6, 2003, now U.S. Pat. No. 7,241,275 issued Jul. 10, 2007, which is a continuation-in-part of U.S. patent application Ser. No. 09/834,438, filed Apr. 13, 2001, now U.S. Pat. No. 6,843,781 issued Jan. 18, 2005, which is a continuation-in-part of U.S. patent application Ser. No. 09/417,671, filed on Oct. 14, 1999, now U.S. Pat. No. 6,494,865, the entire content of each is incorporated herein by reference.

FIELD OF THE INVENTION

The present invention is directed to an intradermal needle that protects a user of an injection device against accidental needle stick injury.

BACKGROUND

Intradermal injections are used for delivering a variety of medicinal substances into a patient. Many of these substances have proven to be more effectively absorbed into, or react with, the immune response system of the body when injected into the intradermal region of the skin (i.e., when injected intradermally). For example, recent clinical trials have shown hepatitis B vaccines administered intradermally are more immunogenic than if administered intramuscularly. In addition, substances have been injected intradermally for diagnostic testing, such as, for example, using what is known in the art as the "Mantoux test" to determine the immunity status of the clinical subject against tuberculosis and the immediate hypersensitivity status of Type I allergic diseases. It is desirable in some instances to provide a prefilled container such as, by way of non-limiting example, a syringe, filled with a medicinal substance and to also provide a needle cannula that may be coupled to the container just prior to administering the injection.

An intradermal injection is made by delivering the substance into the epidermis and upper layer of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, or the epidermis, has a thickness between 500-200 microns, and the dermis, the inner and thicker layer of the skin, has a thickness between 1.5-3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as "wet injection" because of reflux of the substance from the injection site.

Using a standard needle (i.e., one typically used for subcutaneous or intramuscular injections) to deliver an intradermal injection requires the healthcare professional to perform a complicated and sometime difficult technique; with the success of the injection being dependent upon the experience of the healthcare professional and his/her ability to properly execute the technique. The preferred technique (using a standard needle) requires the healthcare professional to stretch the skin, orient the needle bevel to face upwardly, and insert a 26 Gauge short bevel needle cannula to deliver a volume of 0.5 ml or less of the substance into the skin of the patient. The needle cannula is inserted into the skin at an angle varying from around 10-15 degrees so as to form a blister or wheal in which the substance is deposited or otherwise contained. Accordingly, the technique utilized to perform the standard intradermal injection is difficult and requires the attention of a trained nurse or medical doctor. Inserting the needle to a depth greater than about 3.0 mm typically results in a failed intradermal injection because the substance being expelled through the cannula will be injected into the subcutaneous tissue of the patient.

The most frequent cause of a failed intradermal injection results from inserting the needle into the skin at an angle greater than 15 degrees relative to the flattened skin surface. A further cause of error is derived from pinching rather than stretching the skin in the area of the injection, which is normally done when giving a subcutaneous rather than an intradermal injection (pinching increases the likelihood of giving a subcutaneous injection). Procedural errors as described above result in delivering a medicinal substance into the subcutaneous layer, which can reduce the effectiveness of the injection, as well as possibly delivering the substance in a way not approved for delivery.

Intradermal injections performed by using the technique described above also are known to cause a significant amount of pain to the patient because of the angle at which the needle cannula is inserted into the skin. By inserting the needle cannula at that angle, about 5 mm to about 6 mm of the needle is actually inserted into the skin. This results in a significant disruption of the pain receptors dispersed throughout the upper layers of the skin. Also, self-administered intradermal injections are not possible using that technique.

Upon completion of an intradermal injection, shielding and disposal of the contaminated needle cannula becomes a primary concern. Because of the great concern that healthcare professionals and other users may become contaminated by accidental sticks from the needle cannula, it is preferable to cover the contaminated needle as soon as the intradermal injection is completed. As discussed in U.S. Pat. No. 5,893, 845 to Newby et al., for example, the entire content of which is incorporated herein by reference, developments have been made to provide means for covering the contaminated needle cannula upon completion. These devices usually involve some form of shield arrangement that moves in place over the contaminated needle once it has been removed from the patient. However, these shield arrangements often require the use of two hands to perform the operation of moving the shield over the contaminated needle.

Alternatively, needle cannulas with internal or external blunting cannulas have been used that extend from the needle to blunt the distal end. However, these devices require an operation to drive the blunting cannula into position upon completion of the intradermal injection to protect the user from the sharp end of the needle, yet also must allow use without triggering the safety device. In doing so, such devices can require the internal diameter of the needle to be decreased, which may affect flow of the medicinal substance therethrough, or may require the external diameter of the needle to be enlarged, resulting in unnecessary discomfort to the patient.

Numerous other shielding devices also exist, such as those discussed in U.S. Pat. No. 4,631,057 to Mitchell, for example, the entire content of which is incorporated herein by reference. The device disclosed by Mitchell includes a needle cannula guard which is releasably retained in a retracted position, allowing the syringe to be used for injection, and thereafter, lockably retained in the extended position. A similar device is disclosed in U.S. Pat. No. 4,747,837 to Hauck, the entire content of which is also incorporated herein by reference. Hauck discloses a syringe having a cylindrical sheath sleeve which can be advanced to a locked, irreversible position, which prevents further access to the needle cannula tip. Still other shielded designs, such as the device disclosed in U.S. Pat. No. 4,998,920 to Johnson, U.S. Pat. No. 4,801,295 to Spencer, and U.S. Pat. No. 5,053,018 to Talonn et al., the entire content of each being incorporated herein by reference, allows the needle cannula guard to be moved to an extended position through axial movement without locking the guard. However, in this position, the guard can still be moved to expose the sharp needle cannula tip. These devices also require an additional rotation of the needle guard while the guard is fully extended to place it in a locked position.

Other methods of covering the needle cannula include the use of caps located at the distal end of the syringe. As discussed in U.S. Pat. No. 5,496,288 to Niall Sweeney, the entire content of which is incorporated herein by reference, a protective cap attached at a distal end via a hinged member can be constructed to flip using one finger, from a fully closed position covering the needle, to a fully opened position exposing the needle. This allows a healthcare professional who may be holding a patient or medical instrument with one hand to use the other hand to remove the protective cap, administer a partial dose of medicine, and then conveniently place the cap into a protective position.

Other needle cannula devices have shields that are activated during the procedure when the shield comes in contact with the skin. Using the skin to activate the device is not desirable in all applications however, since the device may not activate if the needle does not penetrate sufficiently, or may cause the shield to inadvertently lock when probing. Such devices may also require excessive penetration into some patients to cause the triggering means to activate the device, which can cause a healthcare professional to unnecessarily change their standard method or procedure.

Of still further concern upon completion of such intradermal injections, and as discussed in U.S. Pat. No. 5,674,203 to Lewandoski, the entire content of which is incorporated herein by reference, is the fact that in many areas in a hospital where such needle cannula devices are used, disposal bins are provided so that a syringe or other needle cannula product can be immediately discarded in a safe, rigid container. However, there are areas of medical practice where disposal containers are not readily available or practical. In these areas, products having some form of permanent shielding device are even more desirable. In these areas, permanent shielding after use allows the device to be safely transported to a disposal system.

BRIEF DESCRIPTION OF THE INVENTION

In contrast to the two handed shielding devices and conventional caps discussed above, it has been found by the applicants that safe and secure needle cannula shielding can be performed in connection with the present invention to effectively and reliably secure a cap to a needle cannula assembly after use of the needle cannula using a one handed technique.

In an embodiment of the present invention, an intradermal needle usable with a syringe or similar injection device includes a needle cannula assembly attachable to the syringe, and a cap that provides a secure and sterile enclosure for the needle cannula assembly prior to use, and that also provides a shield within which the needle cannula assembly may be lockably inserted after use to prevent exposure of a tip of a needle cannula thereby significantly reducing the possibility of accidental needle stick injury after use.

The cap includes a forward cap removably matable to a rearward cap, wherein the mated forward and rearward cap enclose the needle cannula assembly therebetween and form a sterile enclosure for storing the needle cannula assembly prior to use.

The rearward cap includes an internal clip to secure the needle cannula assembly in the rearward cap after use of the intradermal needle. Prior to use of the intradermal needle, the forward cap and rearward cap can be separated from each other; with the forward cap and needle cannula still being coupled together. Holding the forward cap, which protectively covers the forward tip of the needle cannula, a user may affix the hub portion of the needle cannula to the syringe. When ready to use, the forward cap may be removed, thereby exposing the forward tip of the needle cannula and rendering the syringe ready to use.

Upon separation of the forward and rearward cap, the rearward cap may be placed on a surface with its open end facing upward, i.e., the distal or open end of the rearward cap being accessible. Upon completion of an injection, the forward tip of the needle cannula may be inserted into the open distal end of the rearward cap, thereby engaging the clip within the rearward cap with a complementary feature defined on the needle cannula assembly to permanently lock the needle cannula assembly and rearward cap together, thus covering the needle cannula.

The present invention thus provides a novel and simple device that significantly reduces the risk of accidental needle stick injury to a patient or healthcare professional, without changing the manner in which an intradermal injection is administered.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1A is a partially exploded perspective view of an intradermal needle constructed in accordance with an embodiment of the present invention, the forward and rearward caps being separated from each other and a needle cannula assembly being held within the forward cap;

FIG. 2 is a perspective view of the needle cannula assembly and forward cap of the present invention coupled to a syringe;

In the drawing figures, it will be understood that like numerals refer to like structures.

DETAILED DESCRIPTION OF EMBODIMENTS OF THE INVENTION

In accordance with embodiments of the present invention, an intradermal needle is provided that includes a needle cannula assembly having a hub, a needle cannula, and a limiter, a cap for housing the needle cannula assembly, and means for locking the needle cannula assembly in a portion of the cap. The cap has a forward cap and a rearward cap to protect and shield a needle cannula prior to and after use. Prior to use, the needle cannula assembly is contained, in a sterile condition, within the forward cap and rearward cap, which are removably mated together. After use, the needle cannula assembly is easily inserted into the rearward cap, which includes a clip for securely and permanently engaging a clip engaging feature defined on the hub of the needle cannula assembly. A forward tip of the needle cannula is thus safely contained within the rearward cap, and the needle cannula assembly is lockingly engaged therein.

Before the needle cannula assembly is used, the healthcare professional removes the rearward cap, which exposes an open end of the hub into which a tip of a syringe may be inserted for locking engagement therebetween. When ready to use, the forward cap is removed, exposing the forward tip of the needle cannula. The rearward cap can be placed on a nearby surface, with the open or distal end of the rearward cap facing upwards.

After use, the rearward cap, which includes a clip, is engaged with a clip engaging feature defined on the hub thereby securely coupling the rearward cap over the forward tip of the needle cannula. The coupling of the clip and clip engaging feature may be accomplished using a one-handed technique. The rearward cap then securely covers the pointed and contaminated (after use) forward tip of the needle cannula, preventing accidental needle sticks and inadvertent cap removal.

As used herein, the term "proximal" refers to a location nearest the person using the intradermal needle or drug delivery device, and farthest from the patient. Conversely, the term "distal" refers to a location farthest from the person using the device and closest to the patient. In addition, the terms "medicinal substance" and "drug" are used in an illustrative and non-limiting manner to generally describe any substance that may be injected into a patient for any purpose. The term "syringe" is also used herein in an illustrative and non-limiting manner to describe a device suitable for delivering a medicinal substance into a patient via injection.

Figure 1B:
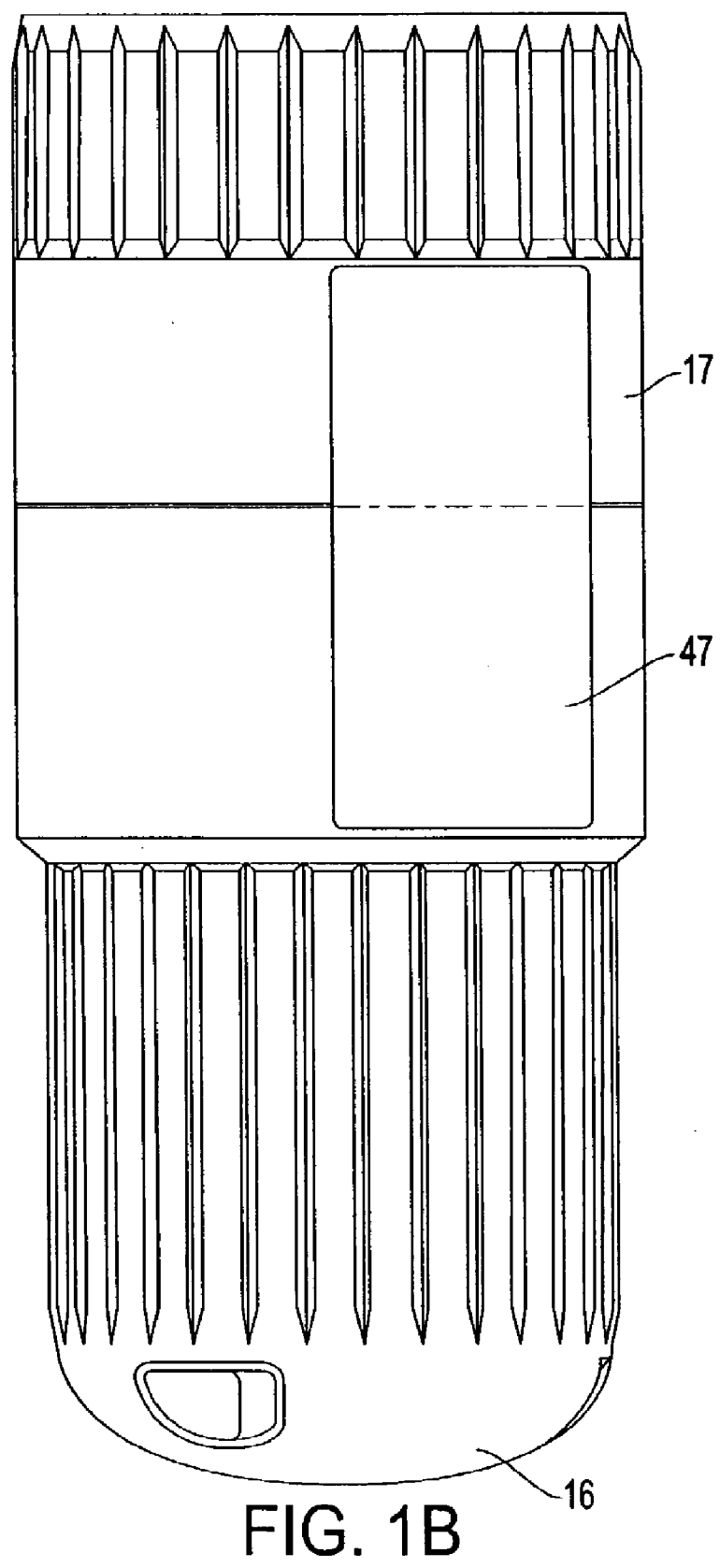
FIG. 1B is perspective view of the intradermal needle of the present invention with the forward and rearward caps mated together.

Referring to FIGS. 1A and 1B, an intradermal needle in accordance with an embodiment of the present invention is there depicted and generally identified by reference numeral 100. The inventive intradermal needle 100 includes a forward cap 16 removably mated with a rearward cap 17, a needle cannula assembly 10 having a limiter portion 12 and a hub portion 14 disposed inside the limiter portion 12, and a needle cannula 36, and means for locking the needle cannula assembly 10 in the rearward cap 17, as described in more detail below. The hub portion 14 includes a throat 18 adapted to receive a syringe 20, as shown in FIG. 2, and as is generally known in the art. The throat 18 may alternatively be adapted to receive other types of drug delivery devices, in accordance with embodiments of the present invention.

The syringe 20 defines a reservoir 21 adapted to store a medicinal substance intended for intradermal delivery. The syringe 20 can be any of a variety of designs such as, for example, a hypodermic syringe, cartridge, pen, and any other delivery device usable to contain and deliver a medicinal substance via injection into a patient. For example, the hub portion 14 might include threads (not shown) for attachment to a pen-type delivery device, or other means for securing the needle cannula assembly 10 to a variety of different drug delivery devices. The syringe 20 depicted in the figures is intended for illustration purposes only, and is not intended to limit the scope or spirit of the present invention.

Figure 3:
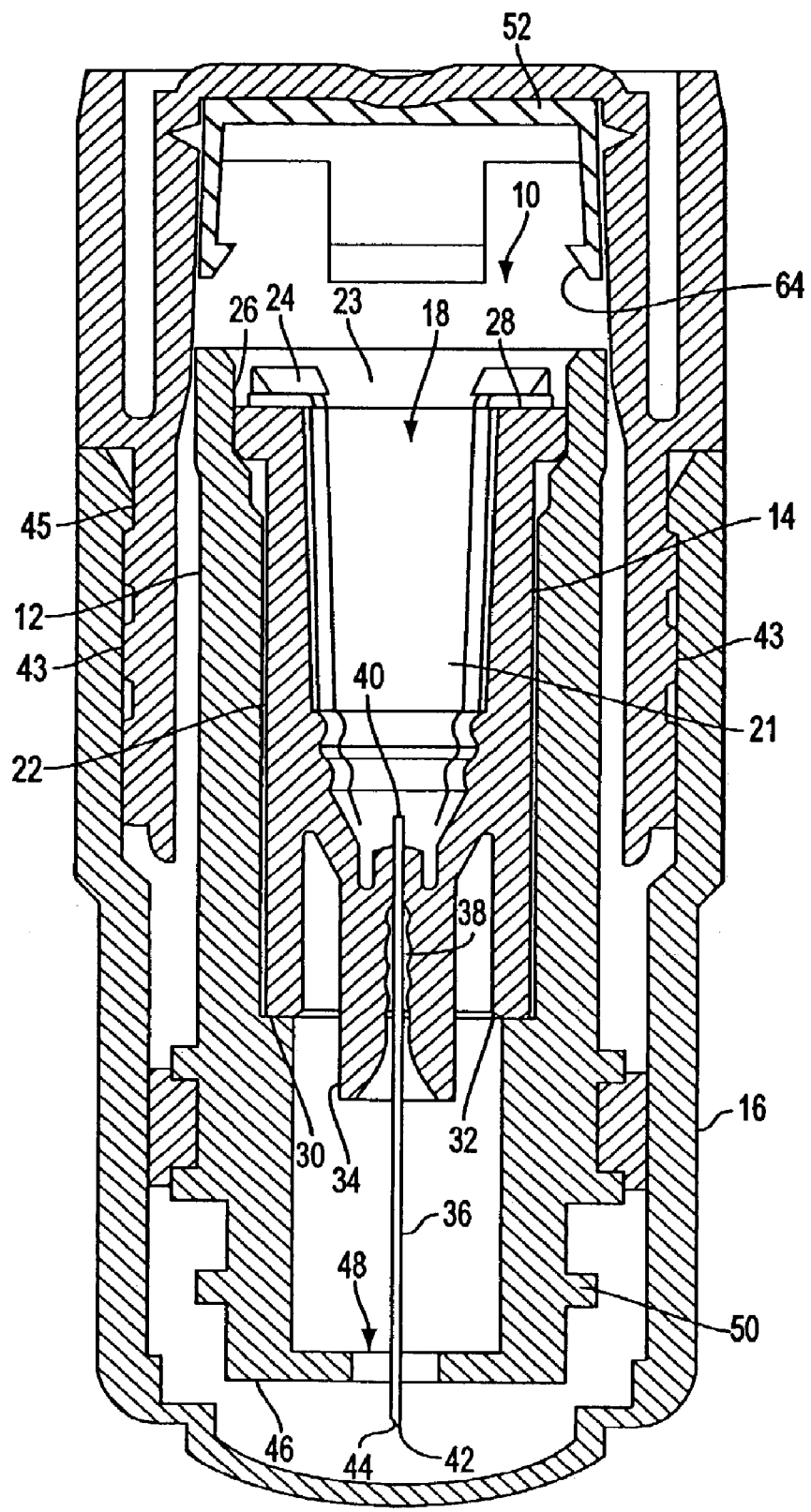
FIG. 3 is a side sectional view of the intradermal needle of the present invention including the assembled forward and rearward cap and needle cannula assembly.

Referring to FIG. 3, the limiter portion 12 defines a tubular chamber 22 wherein the hub portion 14 is received. A plurality of snaps 24 are disposed on a wall 23 of the tubular chamber 22 and clasp a flange 26 circumscribing a rearward end 28 of the hub portion 14 thereby securing the hub portion 14 inside the tubular chamber 22. The tubular chamber 22 includes a ridge 30 that abuts a forward edge 32 of the hub portion 14. The forward edge 32 defines the periphery of hub portion 14. The hub portion 14 defines a sheath 34 that is centrally disposed to the forward edge 32. A needle cannula 36 is received by and fixedly attached to the sheath 34. Preferably, an adhesive 38 fixedly attaches the needle cannula 36 to the sheath 34. More preferably, an epoxy adhesive that is curable with ultraviolet light is used to fixedly attach the needle cannula 36 to the sheath 34. However, other methods of affixing the needle cannula 36 to the sheath 34 may be used such as, by way of non-limiting example, an interference fit.

The needle cannula 36 includes a rearward needle end 40 that extends through the sheath 34 into the throat 18 of the hub portion 14. When the syringe 20 is inserted into the throat 18, the rearward needle end 40 pierces a pierceable member of the syringe (not shown) that seals a distal end of the syringe 20. The rearward needle end 40 is then in fluid communication with the reservoir 21 thereby allowing the substance contained within the reservoir 21 to be expelled through the needle cannula 36 and into the patient. Preferably, the syringe 20 is coupled to the needle cannula assembly 10 just prior to administering the intradermal injection. The throat 18 includes a tapered bottom 21 adapted to securely engage a complementarily shaped feature on the syringe 20, preferably utilizing a Luer-type connection as is well known in the art. Alternatively, a Luer Lok connection (not shown) may be utilized to retain the syringe 20 within the throat 18. As noted above, other means for connecting the needle cannula assembly 10 to the drug delivery device are also contemplated by the present invention, such as, by way of non-limiting example, threaded connection, bayonet connection, and other art-recognized means.

The needle cannula 36 includes a forward tip 42 that is adapted to administer an intradermal injection. Preferably, the forward tip 42 includes a beveled edge 44 having a length ranging from approximately 0.8 mm to 1.0 mm. More preferably, the beveled edge 44 is approximately 0.9 mm in length. A standard bevel tip length (i.e., for non-intradermal injections) ranges from approximately 1.3 mm to 1.6 mm. The reduced length of the beveled edge 44 of the present invention reduces the potential of the needle cannula 36 passing through the dermis layer of the skin of the patient and resulting in undesirable injection into the subcutaneous region. The reduced length of the beveled edge 44 also reduces the potential for leakage of the medicinal substance from the site of the injection.

The limiter portion 12 surrounds the needle cannula 36 and extends away from the hub portion 14 toward the forward tip 42 of the needle cannula 36. The limiter portion 12 preferably includes an aperture 48 through which the needle cannula 36 passes, with or without contacting interference between the limiter portion 12 and needle cannula 36. The limiter portion 12 also includes a generally flat skin engaging surface 46 extending in a plane that is generally perpendicular to a longitudinal axis of the needle cannula 36 within about fifteen degrees of perpendicular, or more preferably, within about five degrees of perpendicular. The skin engaging surface 46 is adapted to be received against the skin of the patient during administration of an intradermal injection and provides for a stable placement of the needle cannula 36 against the patient's skin. When the hub portion 14 is inserted into the limiter portion 12, the needle cannula 36 passes through the aperture 48. Thus, only the length of the needle cannula 36 extending through the aperture 48 is available to be inserted into the skin of the patient.

Figure 4:
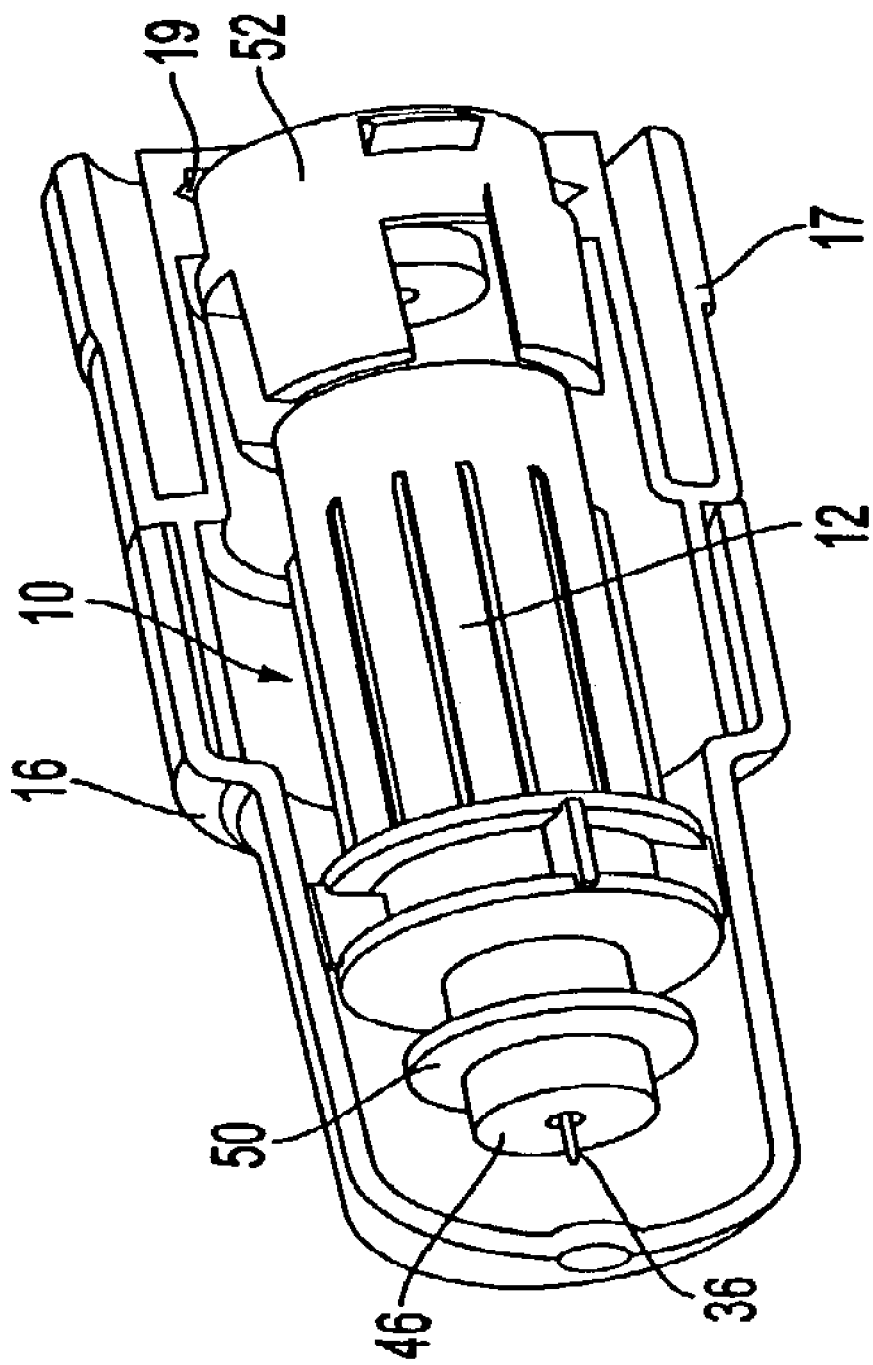
FIG. 4 is a partial cross-sectional perspective view of the intradermal needle of the present invention.
Figure 5:
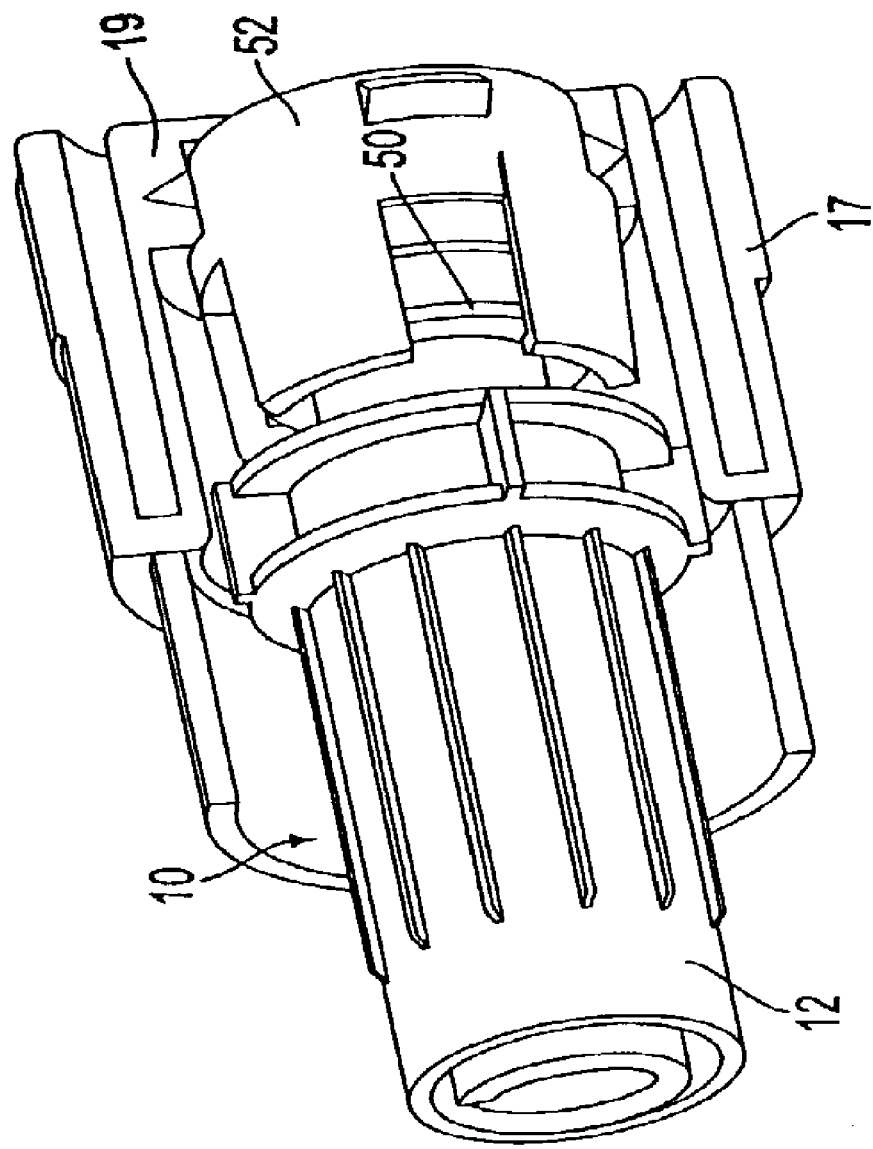
FIG. 5 is a partial cross-sectional perspective view of the rearward cap with the needle cannula assembly lockingly secured therein so as to shield the tip of the needle cannula.

As shown in FIGS. 3, 4 and 5, the limiter portion 12 surrounds the needle cannula 36 and extends away from the hub portion 14 toward the forward tip 42 of the needle cannula 36, as described above. The skin engaging surface 46 preferably has a diameter of 5 mm to 20 mm, most preferably, a diameter of 5.5 mm. The limiter portion 12 also includes an annular rib 50 extending about an outside circumference of the limiter portion 12 and spaced apart in a proximal direction from the skin engaging surface 46. The rib 50 may be continuous about the limiter portion 12, or it may be segmented. Other rib 50 configurations and constructions are also contemplated by and within the scope and spirit of the present invention. The rib 50 engages a complementarily shaped feature in the rearward cap 17 to lockingly secure the needle cannula assembly 10 and rearward cap 17 after use of the needle cannula assembly 10, as described in greater detail below.

The forward tip 42 of the needle cannula 36 extends beyond the skin engaging surface 46 a distance of approximately 0.5 mm to 3.0 mm and preferably about 1.0 to 2.0 mm, and more preferably 1.5 mm±0.2 to 0.3 mm. The length the needle cannula 36 extends beyond the skin engaging surface 46 is determined by the position of the ridge 30 relative to the skin engaging surface 46 as shown in FIG. 3. Therefore, the limiter portion 12 limits penetration of the needle cannula 36 so that the medicine or drug substance is injected only into the dermis layer of the patient.

Referring once again to FIGS. 1A, 1B and 3, the forward and rearward cap 16 and 17, together contain and conceal the forward tip 42 of the needle cannula 36 of the needle cannula assembly 10 prior to use and also provide a sterile container for the needle cannula assembly 10. The rearward cap 17 mates to the forward cap 16 and is removably secured with an interference fit provided by a plurality of annular ribs 43 disposed upon a surface of the rearward cap 17 and abutting the forward cap 16. The forward cap 16 includes an annular protuberance 45 positioned opposite the annular ribs 43 providing a snapping action when the forward cap 16 and the rearward cap 17 are mated, thereafter providing a sanitary and sterile enclosure for the needle cannula assembly 10. To ensure the needle cannula assembly 10 has not been accessed prior to use, a tamper indicator strip 47 is positioned over a seam formed between the mated caps 16 and 17. The strip 47 is perforated along the seam, and a ripped or torn perforation indicates that the forward and rearward cap 16 and 17 have been opened and that the needle cannula assembly 10 may no longer be sanitary. Additionally, as described in greater detail below, the rearward cap 17 provides a locking enclosure for the contaminated needle cannula assembly 10 after use.

As discussed above, after use of an injection device of the type described herein, the healthcare professional will normally dispose of the injection device, including a needle cannula, in a sharps collector, following U.S. Centers For Disease Control and Prevention (CDC) guidelines. If this is not possible, for example, due to the absence or lack of proximity to a sharps collector, then the risk of needle stick injury is significantly increased. In such cases, it is necessary to shield the needle cannula after use of the injection device.

In an embodiment of the present invention, the forward and rearward cap 16 and 17 first provide a sterile enclosure for the needle cannula assembly 10 prior to use. Removing the rearward cap 17 allows the coupling of a syringe 20 to the hub portion 14, while the forward cap 16 removably shields the needle cannula 36 during coupling of the syringe 20 and hub portion 14. Once the hub portion 14 is coupled to the syringe 20, the forward cap 16 is removed thereby exposing the needle cannula 36 for use. After use, the forward tip 42 of the needle cannula 36 is placed into the rearward cap 17, with the rib 50 and clip 52 (discussed in more detail below) locking the rearward cap 17 and needle cannula assembly 10, permanently shielding the forward tip 42 of the needle cannula 36.

In FIGS. 3 and 4, the rearward cap 17 and needle cannula assembly 10 are shown in a first orientation, or an orientation prior to administering the intradermal injection. In FIGS. 3 and 4, the forward cap 16 is mated with the rearward cap 17, and is removably secured to the limiter portion 12 of the needle cannula assembly 10 with an interference fit. Prior to use, the rearward cap 17 is separated from the forward cap 16, with the needle cannula assembly 10 being removably held by the forward cap 16. The hub portion 14 is then coupled to the syringe 20, and the forward cap 16 removed exposing the forward tip 42 of the needle cannula 36 and rendering the injection device ready for use. Subsequent to use of the injection device, the user inserts the forward tip 42 of the needle cannula 36 into the open end of the rearward cap 17, previously placed on a surface proximal to the user during administration of the injection. As the forward tip 42 of the needle cannula 36 is inserted into the rearward cap 17, the rib 50 defined about the limiter 12 engages the clip 52, placing the needle cannula assembly 10 and rearward cap 17 in a second orientation, as shown in FIG. 5. The rearward cap 17 and clip 52 are thus securely engaged with the rib 50 of the limiter portion 12 and fully cover the forward tip 42 of the needle cannula 36 for safe handling and disposal after use. As described in greater detail below, the rearward cap 17 and needle cannula assembly 10 are locked together, and cannot be easily separated.

The rearward cap 17 and needle cannula assembly 10 are lockingly engaged with each other by the complementarily structured clip 52 and rib 50. While an embodiment of the clip 52 and rib 50 is disclosed herein, the present invention also contemplates other embodiments that function in a similar manner to lockingly engage the rearward cap 17 and needle cannula assembly 10. The clip 52 is secured within the rearward cap 17, as can be seen in FIGS. 3 and 4. In an embodiment of the present invention, the clip 52 includes a plurality of raised profiles 56a, which engage a recess 19 or other complementary structure defined within the rearward cap 17. Threaded, snap-fit, or other manners of engagement between the raised profiles 56a and recess 19, for example, are contemplated by, and within the scope and spirit of the present invention, as are other means for securing the clip 52 within the rearward cap 17. The clip 52, once secured within the rearward cap 17, is used to grasp the rib 50 when the rearward cap 17 is engaged with the needle cannula assembly 10. The clip 52 and rib 50 thus secure the rearward cap 17 to the needle cannula assembly 10 and, thereafter, prevent separation of those parts.

Figure 6:
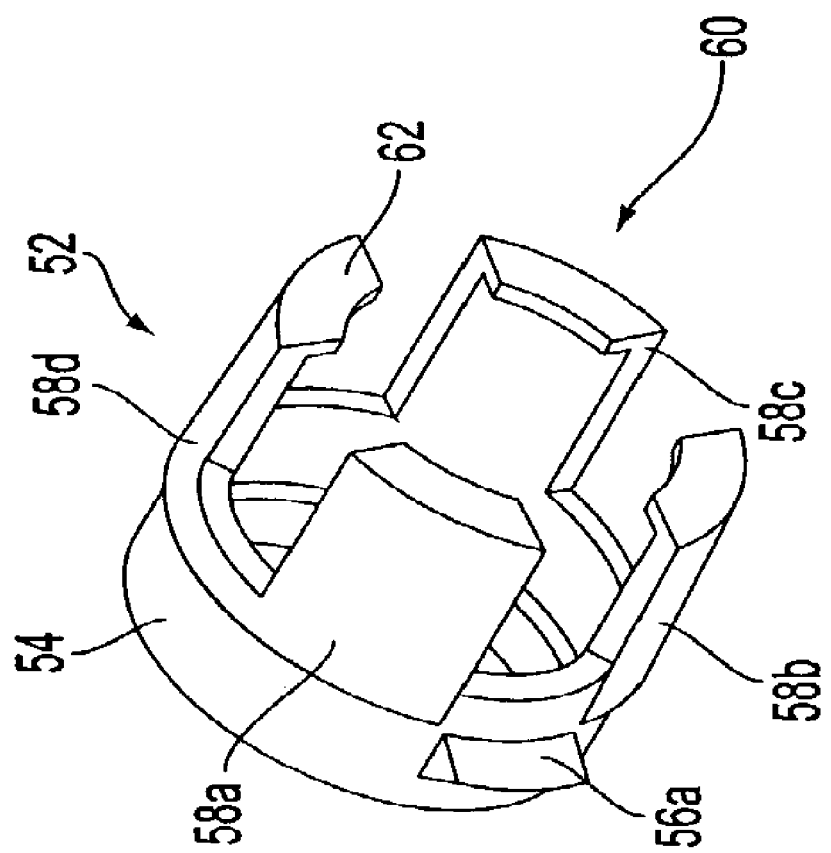
FIG. 6 is an enlarged perspective view of the locking clip of the present invention.

As shown in FIG. 6, the clip 52 includes a generally cylindrical body 54 having an outside diameter sufficient to securely fit within the rearward cap 17, and to allow engagement between a number of raised thread profiles, such as 56a (shown) and an engagement mechanism (e.g., recess 19 depicted in FIG. 4) located within the rearward cap 17. A series of radially disposed flanges 58a-58d extend from the clip body 54 and define an opening 60. The flanges 58a-58d extend without interference with the proximal end of the needle cannula assembly 10 when the needle cannula assembly 10 and rearward cap 17 are in the first orientation, shown in FIG. 4. The flanges 58a-58d receive and engage the distal end of the needle cannula assembly 10 when the needle cannula assembly 10 and rearward cap 17 are in the second orientation, shown in FIG. 5. Each flange 58a-58d includes a lip 62, located at a free end of each flange 58a-58d, and which defines an inner diameter of opening 60. The lip 62 has a tapered surface 64 (see, e.g., FIG. 3) over which the rib 50 can easily pass during engagement of the needle cannula assembly 10 and rearward cap 17. During engagement between the rearward cap 17 and the needle cannula assembly 10, flanges 58a-58d deflect slightly outward allowing the lip 62 to travel over the rib 50. Upon complete engagement between the rearward cap 17 and the needle cannula assembly 10, flanges 58a-58d return to a non-deflected position and secure the lip 62 of each flange behind the rib 50, locking the clip 52 and rearward cap 17 in place at the distal end of the needle cannula assembly 10. In the embodiment described above, the clip 52 can be constructed of any suitable material, such as plastic or metal, and can be constructed to screw into the rearward cap 17 as described above, or snap into a series of undercuts in the cap.

As described above, once within the rearward cap 17, the clip 52 is configured to engage the limiter portion 12 when the rearward cap 17 and the distal end of the needle cannula assembly 10 are firmly pressed together. One method to achieve this in accordance with an embodiment of the present invention is with a one-handed capping technique. Before the needle cannula assembly 10 is used, the healthcare professional first removes and separates the forward and rearward cap 16 and 17, and places the rearward cap 17 on a nearby surface with the open distal end of the rearward cap 17 facing upwards. After use, the distal end of the needle cannula assembly 10 is inserted into the open distal end of the rearward cap 17, until the rib 50 engages the clip 52, thereby locking the used needle cannula assembly 10 in the rearward cap 17. Once secured, the rearward cap 17 is permanently locked to the needle cannula assembly 10, protecting the healthcare professional against needle stick injury from the contaminated forward tip 42 of the needle cannula 36.

Such a technique as described above and defined by the U.S. Occupational Safety and Health Administration (OSHA) as recapping a contaminated needle, is discussed in OSHA Regulation 29 CFR 1910.1030(d)(2)(vii)(B), the entire content of which is incorporated herein by reference. Specifically, the requirement states, such bending, recapping or needle removal must be accomplished through the use of a mechanical device or a one-handed technique, such as described above, by placing an open cap on a surface, and directing the contaminated needle cannula into the cap using one hand. Such one handed methods are intended for protecting the second hand from needle contact.

The embodiments of the present invention described herein effectively and safely cover a needle prior to, and subsequent to, use. The forward and rearward cap of the present invention together form a hard packaging unit that contains the needle and acts as an effective sterility barrier prior to use of the needle cannula assembly as part of a drug delivery device for administering the intradermal injection. One the needle cannula assembly is secured to a syringe, for example, the forward cap forms a removable protective barrier prior to use, and the rearward cap forms a hard packaging unit that contains the needle and acts as an irremovable protection barrier subsequent to use. As noted above, the health care professional will normally dispose of the syringes in a sharps collector, however if this is not possible, the embodiment of the present invention described above can be used as an alternate, or backup system.

The invention has been described in an illustrative manner, and it is to be understood that the terminology which has been used is intended to be in the nature of words of illustration rather than of limitation. Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. An intradermal needle comprising:
   a needle cannula assembly comprising:
      a hub portion;
      a needle cannula held by said hub portion and having a forward tip extending away from said hub portion;
      a limiter portion surrounding said needle cannula and extending away from said hub portion toward said forward tip of said needle cannula, said limiter including a generally flat skin engaging surface extending in a plane generally perpendicular to a longitudinal axis of said needle cannula, said needle cannula forward tip extending beyond said skin engaging surface;
   a forward cap, having a closed end;
   a first orientation of the hub and needle cannula wherein the forward tip is pointing toward the closed end of the forward cap; and,
   a rearward cap adapted to be removably matable to said forward cap and having at least one locking lug adapted for engagement to said limiter, wherein said at least one locking lug and said limiter are complementary so as to lockingly engage said needle cannula assembly in said rearward cap by an inversion of the hub from the first orientation after use of said intradermal needle whereby said needle cannula assembly is lockingly held at least partially within said rearward cap and said forward tip of said needle cannula is entirely contained within said rearward cap.

2. An intradermal needle as set forth in claim 1, wherein said limiter further comprises a rib defined about said limiter and wherein said at least one locking lug to engage said rib.

3. An intradermal needle as set forth in claim 2, wherein said rib comprises a continuous annular rib defined about said limiter.

4. An intradermal needle as set forth in claim 2, wherein said at least one locking lug is a plurality of radially disposed lugs to engage said rib.

5. An intradermal needle as set forth in claim 1, wherein said forward cap has a closed distal end and an open proximal end, said open proximal end being sized and shaped to mate with said rearward cap, said needle cannula being located in proximity to said closed distal end prior to use of said intradermal needle.

6. An intradermal needle as set forth in claim 1, wherein said forward cap and said rearward cap form a sterile enclosure for said needle cannula assembly.

7. An intradermal needle as set forth in claim 1, wherein said forward tip of said needle cannula extends away from said hub portion a distance of not greater than 3 mm.

8. An intradermal needle as set forth in claim 7, wherein said forward tip of said needle cannula extends away from said hub portion a distance ranging from 1 mm to 2 mm.

9. An intradermal needle as set forth in claim 8, wherein said forward tip of said needle cannula extends away from said hub portion a distance of 1.5 mm, ±0.2 to 0.3 mm.

10. An intradermal needle as set forth in claim 1, wherein said skin engaging surface has a diameter ranging from 5 mm to 20 mm.

* * * * *